(12) United States Patent
Morris (10) Patent No.: US 8,733,841 B2
(45) Date of Patent: May 27, 2014

(54) ZERO TURN LAWNMOWER MOUNTING SUPPORT ARM

(76) Inventor: Daniel L. Morris, Poultney, VT (US)

( * ) Notice: Subject to any disclaimer, the term of this patent is extended or adjusted under 35 U.S.C. 154(b) by 81 days.

(21) Appl. No.: 13/506,706

(22) Filed: May 11, 2012

(65) Prior Publication Data

US 2013/0299650 A1    Nov. 14, 2013

(51) Int. Cl.
  *A47C 7/54*    (2006.01)
(52) U.S. Cl.
  USPC .............. 297/411.36; 297/411.35; 248/201
(58) Field of Classification Search
  USPC .......... 248/201; 297/411.32, 411.33, 411.35, 297/411.36, 411.38; 108/116
  See application file for complete search history.

(56) References Cited

U.S. PATENT DOCUMENTS

| | | | | |
|---|---|---|---|---|
| 2,592,702 A * | 4/1952 | Sprung | ................ | 297/411.32 |
| 2,655,981 A * | 10/1953 | Nichols et al. | ................ | 297/323 |
| 3,206,249 A * | 9/1965 | Gateley | ................ | 297/411.23 |
| 3,858,905 A | 1/1975 | Peebles | | |
| 4,420,164 A * | 12/1983 | Mitchell | ................ | 280/293 |
| 5,046,582 A | 9/1991 | Albrecht | | |
| 5,237,932 A | 8/1993 | Edwsards | | |
| 5,305,773 A * | 4/1994 | Browning | ................ | 135/67 |
| 5,359,741 A * | 11/1994 | Lang | ................ | 5/507.1 |
| 5,509,432 A * | 4/1996 | Peterson | ................ | 135/65 |
| 5,517,809 A | 5/1996 | Rich | | |
| 5,644,994 A * | 7/1997 | Liang et al. | ................ | 108/116 |
| 5,647,451 A | 7/1997 | Reichel | | |
| 5,979,857 A * | 11/1999 | Holm | ................ | 248/451 |
| 6,003,633 A | 12/1999 | Rolson | | |
| 6,059,366 A * | 5/2000 | Hu | ................ | 297/411.35 |
| 6,076,787 A * | 6/2000 | Troyer | ................ | 248/166 |
| 6,116,378 A | 9/2000 | Barrow | | |
| 6,206,468 B1 * | 3/2001 | Brosnan et al. | ................ | 297/228.1 |
| 6,488,157 B2 * | 12/2002 | Chen | ................ | 211/20 |
| 6,543,733 B1 * | 4/2003 | Pennington | ................ | 248/149 |
| 6,615,744 B1 * | 9/2003 | Eckstein et al. | ................ | 108/147.2 |
| 6,676,578 B2 * | 1/2004 | Lindqvist | ................ | 482/142 |
| 6,802,493 B2 * | 10/2004 | Lance | ................ | 254/131 |
| 6,860,281 B1 * | 3/2005 | Clift | ................ | 135/67 |
| 6,935,093 B2 | 8/2005 | Velke et al. | | |
| 7,047,716 B2 | 5/2006 | Lang | | |
| 7,156,465 B2 * | 1/2007 | Stewart et al. | ................ | 297/411.36 |
| 7,174,993 B2 | 2/2007 | Lantz | | |
| 7,296,787 B2 * | 11/2007 | Barrios et al. | ................ | 269/17 |
| 7,341,006 B2 * | 3/2008 | Hernandez | ................ | 108/115 |
| 7,448,606 B1 * | 11/2008 | Johnson | ................ | 269/17 |

(Continued)

OTHER PUBLICATIONS

Handrail Used for Portable Work Platform, Senda Toyoji, Application #: JP20102159629 Publication date: Jul. 22, 2010.

*Primary Examiner* — Terrell McKinnon
*Assistant Examiner* — Daniel J Breslin
(74) *Attorney, Agent, or Firm* — John J. Welch, Jr., Esq.

(57) ABSTRACT

A zero turn lawnmower mounting support arm affixable to the frame assembly portion of the lawnmower and being made up of a mounting tube unit affixed to the topside of the frame assembly and to which a first hollow tube unit is perpendicularly affixed with a laterally positioned mounting plate being also affixed to the frame assembly and the mounting tube and the first hollow tube unit with a second hollow tube unit atop of which there is held a pivotable handrest base unit equipped with a cushion and pivot arm stop complex unit with the second hollow tube unit being adjustably fitted about the first hollow tube unit.

12 Claims, 9 Drawing Sheets

(56) References Cited

U.S. PATENT DOCUMENTS

| | | | |
|---|---|---|---|
| 7,631,604 B2* | 12/2009 | Huang | 108/116 |
| 7,726,729 B2* | 6/2010 | Groll | 297/4 |
| 7,775,228 B2* | 8/2010 | Clark | 135/66 |
| 7,782,554 B1* | 8/2010 | Griffin | 359/802 |
| 7,988,137 B2* | 8/2011 | Johnson | 269/16 |
| 8,128,172 B2* | 3/2012 | Tsai | 297/411.36 |
| 8,245,856 B1* | 8/2012 | Pappin et al. | 211/13.1 |
| 8,302,738 B2* | 11/2012 | Sorensen | 187/203 |
| 8,360,252 B1* | 1/2013 | Fagan | 211/21 |
| 8,479,337 B1* | 7/2013 | Morris | 14/71.1 |
| 2005/0223486 A1* | 10/2005 | Jumalon | 4/619 |
| 2006/0191448 A1* | 8/2006 | Chen et al. | 108/125 |
| 2006/0278472 A1 | 12/2006 | Kenton et al. | |
| 2010/0139228 A1 | 6/2010 | Sugio et al. | |
| 2010/0154373 A1 | 6/2010 | Newell | |
| 2011/0185692 A1 | 8/2011 | Marshall et al. | |

* cited by examiner

ZERO TURN LAWNMOWER MOUNTING SUPPORT ARM

FEDERALLY SPONSORED RESEARCH AND DEVELOPMENT

The invention is not the product of any federally sponsored research and development.

PRIOR OR PARENT APPLICATIONS

The invention is not the subject of any prior or parent applications for Letters Patent.

BACKGROUND OF THE INVENTION a. Field of the Invention

The invention relates to that coterie of devices that are attachable to motorized "sit down" lawnmower units.

b. Related Art

The art disclosed in the Informational Disclosure Statement hereby submitted related to but does not anticipate the invention.

A SUMMARY OF THE INVENTION a. A Brief Description of the Invention

The invention is a mounting support arm that is attached to a "sit down" riding motorized lawnmower unit. Typically, it is attached to so-called "zero turn" tractor variants of such lawnmower units. The invention is made up of the following components held in combination with one another for attachment ultimately to such a lawnmower unit. The first of such components is a mounting tube unit typically hollow and rectangularly shaped and affixed to the topside of a lateral portion of the frame assembly of the lawnmower unit. One such mounting tube unit is affixed to one lateral portion, and, another is affixed to the other lateral portion of the frame assembly, whereas, the lawnmower unit would, ultimately, be fitted with two (2) equivalent and oppositely positioned mounting support arms. Each such mounting tube has a plurality of paired vertically inclined holes for receipt of self tapping screws for purposes of securely affixing each mounting tube, via holes drilled into the topsides of each lateral portion, to each such lateral portion. A first typically, rectangularly shaped hollow tube unit is perpendicularly affixed to each mounting tube. A laterally positioned multisided mounting plate is affixed to each conjoined mounting tube unit and first hollow tube unit and is likewise affixed to the lateral walling of each lateral portion of the frame assembly. Holes are drilled into the mounting plate and the lateral walling of each lateral portion. Such holes are horizontally inclined for receipt of self tapping screws as affixation means. The first hollow tube unit has a plurality of horizontally inclined paired holes in each lateral side thereof. A second also rectangularly shaped hollow tube unit with internal diagonal breadth in excess of that of the first hollow tube unit is fittable from above, about the first hollow tube unit. The second hollow tube unit has a lower pair of horizontally inclined holes in each lateral side thereof amenable to receipt of a positioning pin receivable by each and, as well, any one pair of the plurality of paired holes in the first hollow tube unit, all as a means of adjusting the overall height of the mounting support arm. There is also an upper pair of horizontally inclined holes in the second hollow tube unit. There is a three sided, typically rectangularly shaped pivotable handrest base unit. The handrest base unit has, near the posterior end thereof, a pair of horizontally inclined holes, one in each side thereof. The handrest base unit is connected to the uppermost portion of the second hollow tube unit via a pivot pin complex insertable through the base unit holes and the upper pair of horizontally inclined holes in the second hollow tube unit of each mounting support arm. A four sided hand cushion unit is affixed to the topside of the handrest base unit. Internally affixed within the handrest base unit at the posterior end thereof is a pivot stop complex being a small plate unit with a threaded hole in it through which there is positioned a threaded bolt combined with an adjustable nut. The stop complex serves to determine the least angle of static positioning of the handrest base unit with affixed cushion unit with respect to the hollow tube units.

b. Objects of the Invention

The invention is intended to serve the needs and wishes of handicapped persons in their efforts to mount motorized zero turn lawnmower devices. Such handicapped persons utilizing the invention, and seeking to mount such devices, would be persons such as would have been afflicted with, for example, Multiple Sclerosis, but who would however be left with, at least, some partial motility potential as regards their lower limb motor capabilities. Typically such persons are those who would be wheelchair-bound and who might wish to mount such devices after having embarked from their wheelchairs atop a platform of sorts below one side of which would be found such a lawnmower device amenable to being driven out and away from below the platform and then back again. However, absent resort to utilization of the mounting arms such as are the subject of the present application, as a means for facilitating any mounting on the part of such persons of such devices, such efforts on the part of such persons would be, at the very least, very difficult and unquestionably quite risky from a personal safety vantage point. Moreover, the same holds true as respects efforts on the part of such persons to thereafter dismount from such devices and reenter their respective wheelchairs remaining atop the platform.

The personal safety of such persons in respect of their efforts to mount and later dismount from such devices is greatly enhanced by the presence of the invented arms affixed to such devices as disclosed herein.

Your Inventor, respectfully submitted, can readily attest to the fact of such enhancement, since, he is, himself, just such a handicapped person who has caused a pair of his invented mountain support arms to be affixed to his own zero turn lawnmower, and; mounting and dismounting on his part from such devices is unquestionably much safer with resort to use of the arms.

A DESCRIPTION OF THE PREFERRED EMBODIMENT

Figure 1:
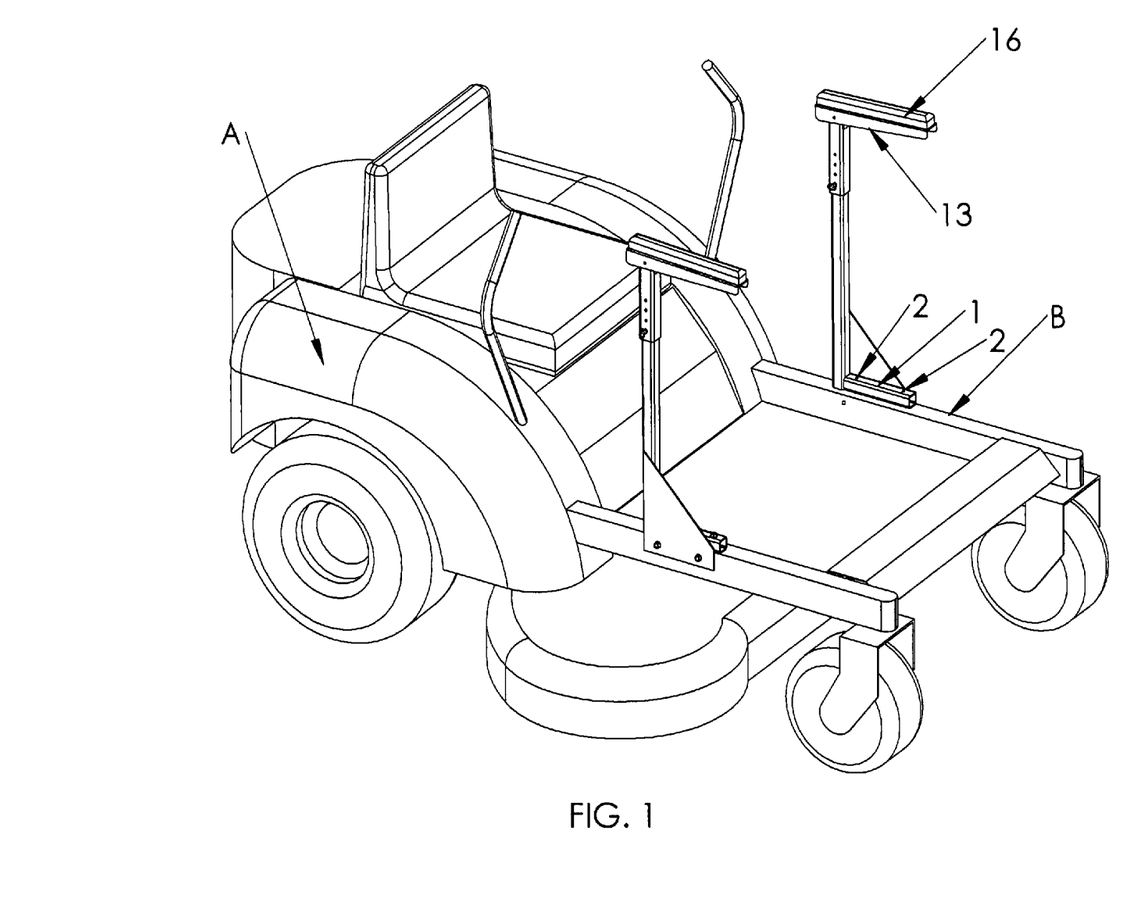
FIG. 1 is a depiction of a zero turn lawnmower device being shown equipped with a pair of the invented mounting support arms.
Figure 2:
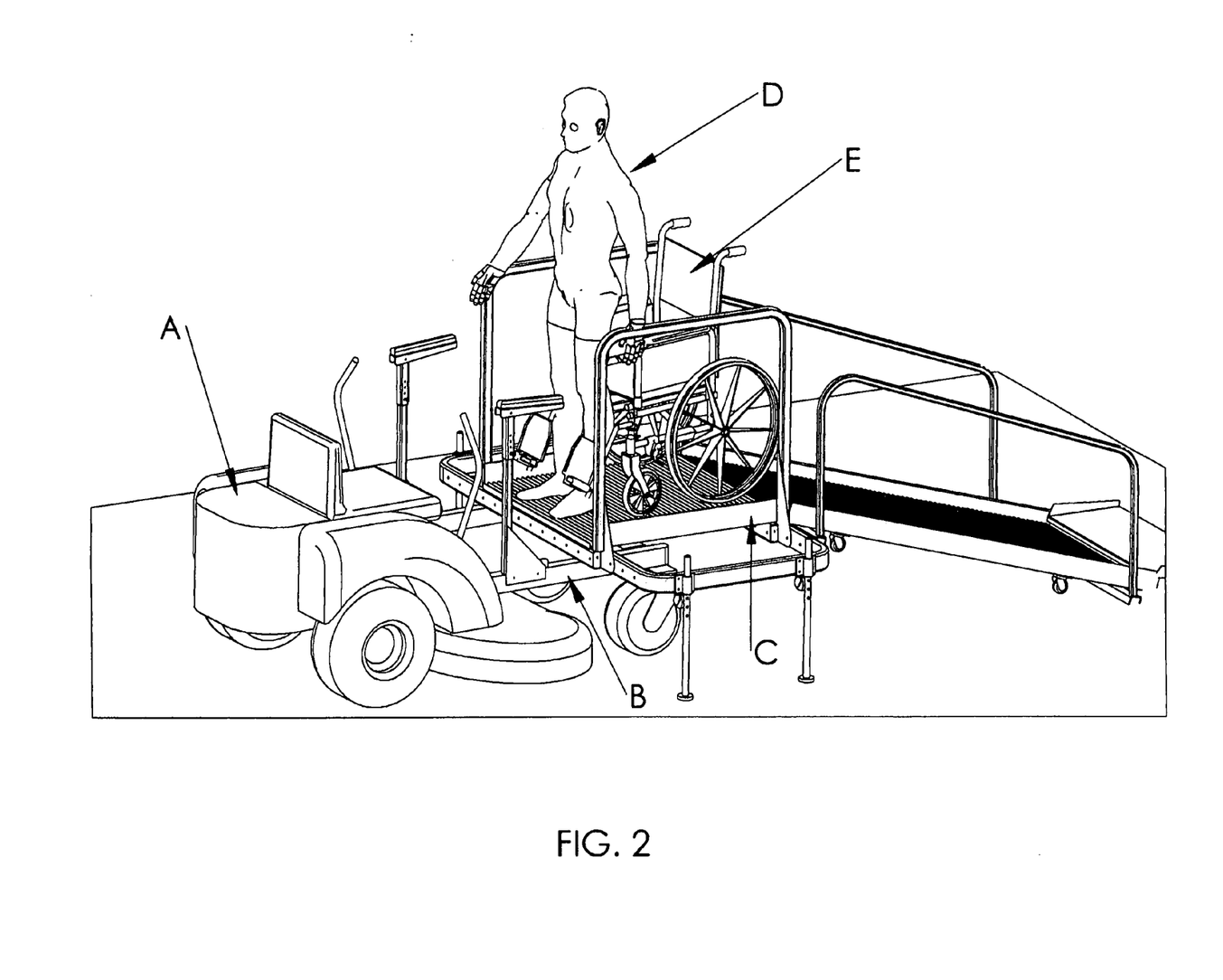
FIG. 2 shows the so-equipped lawnmower device in the presence of a platform atop of which is a person disembarking from a wheelchair seeking to mount the device.
Figure 3:
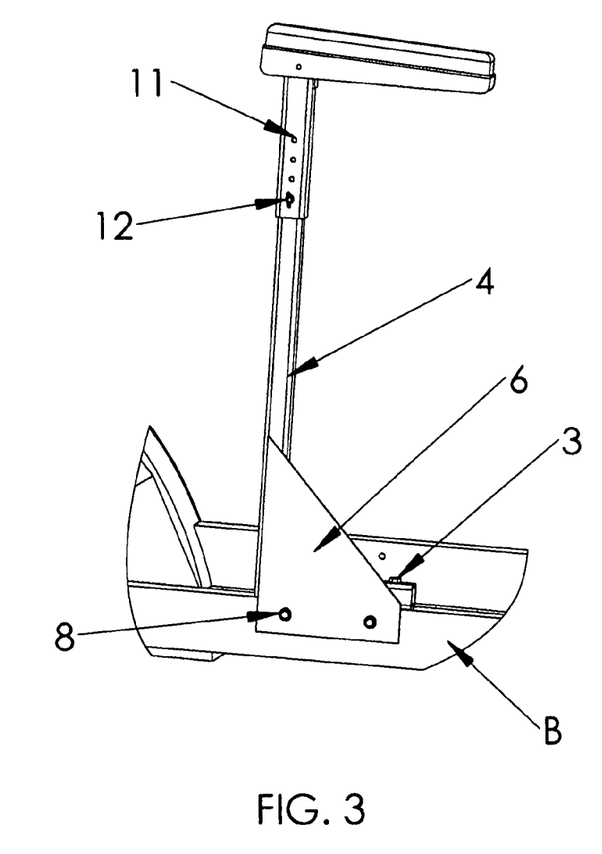
FIG. 3 is a laterally oriented, isolated perspective view of a mounting support arm affixed to the frame assembly portion of a zero turn lawnmower device.
Figure 4:
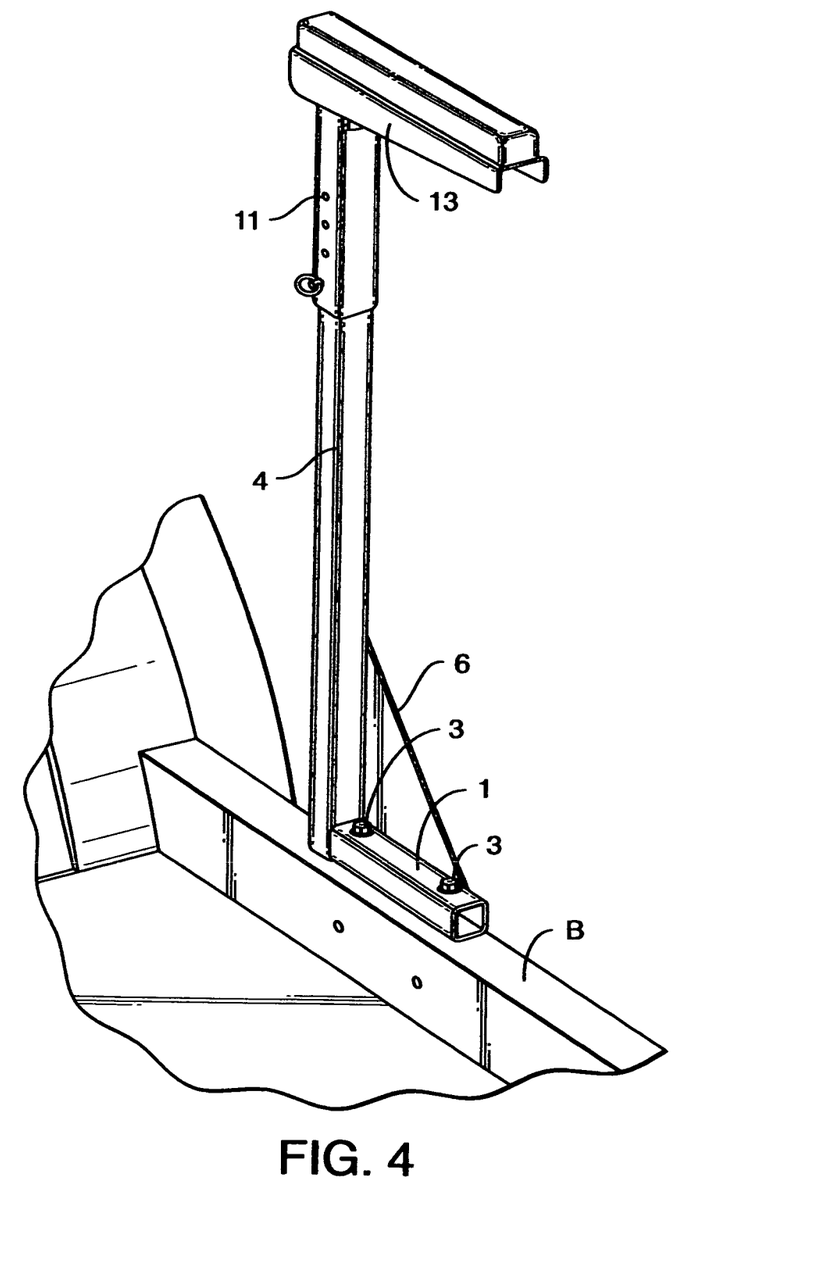
FIG. 4 is a medially oriented, isolated perspective view of a mounting support arm affixed to the frame assembly portion of a zero turn lawnmower device.
Figure 5:
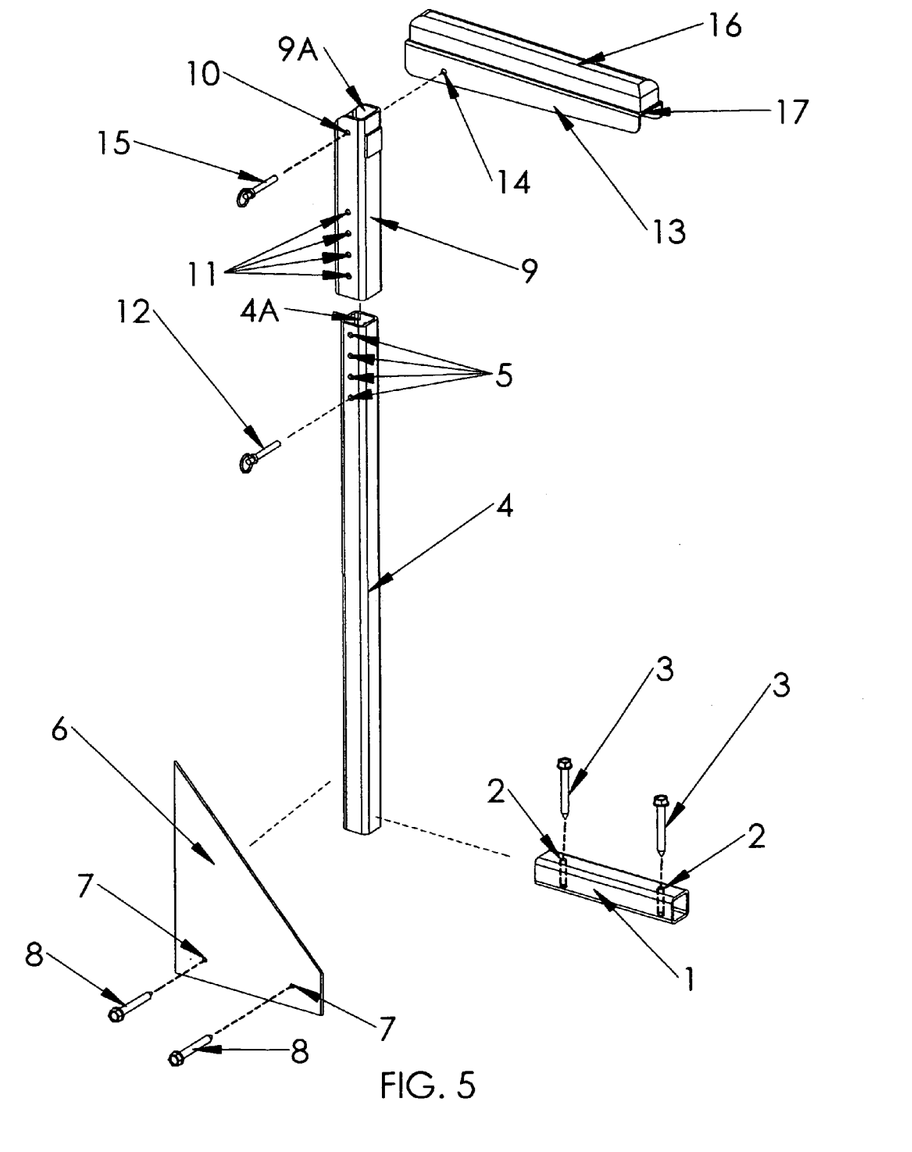
FIG. 5 is an exploded view of the various component parts of the invented mounting support arm including the first variant of the base unit cushion component of the invention.
Figure 7:
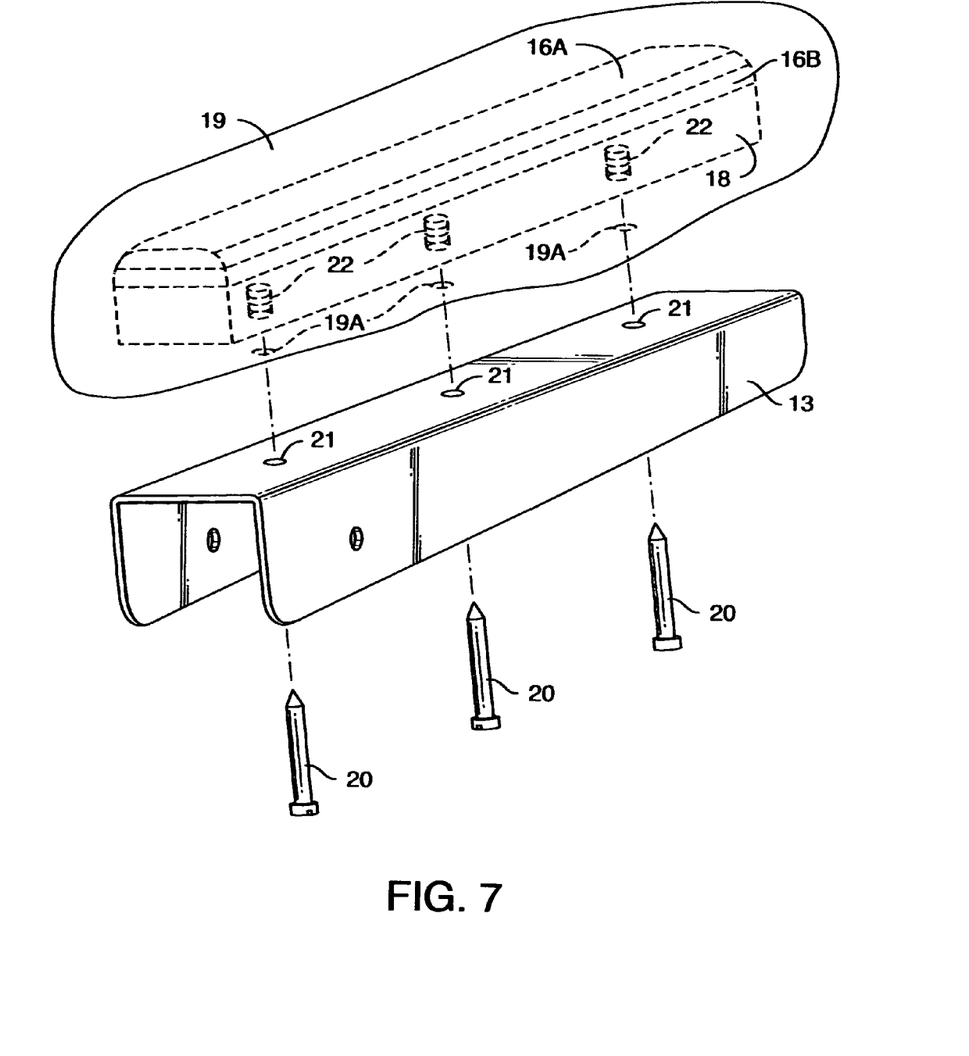
FIG. 7 is an exploded view of the second variant of the base unit cushion component of the invention, in apposition to the pivotable handrest base unit.
Figure 8:
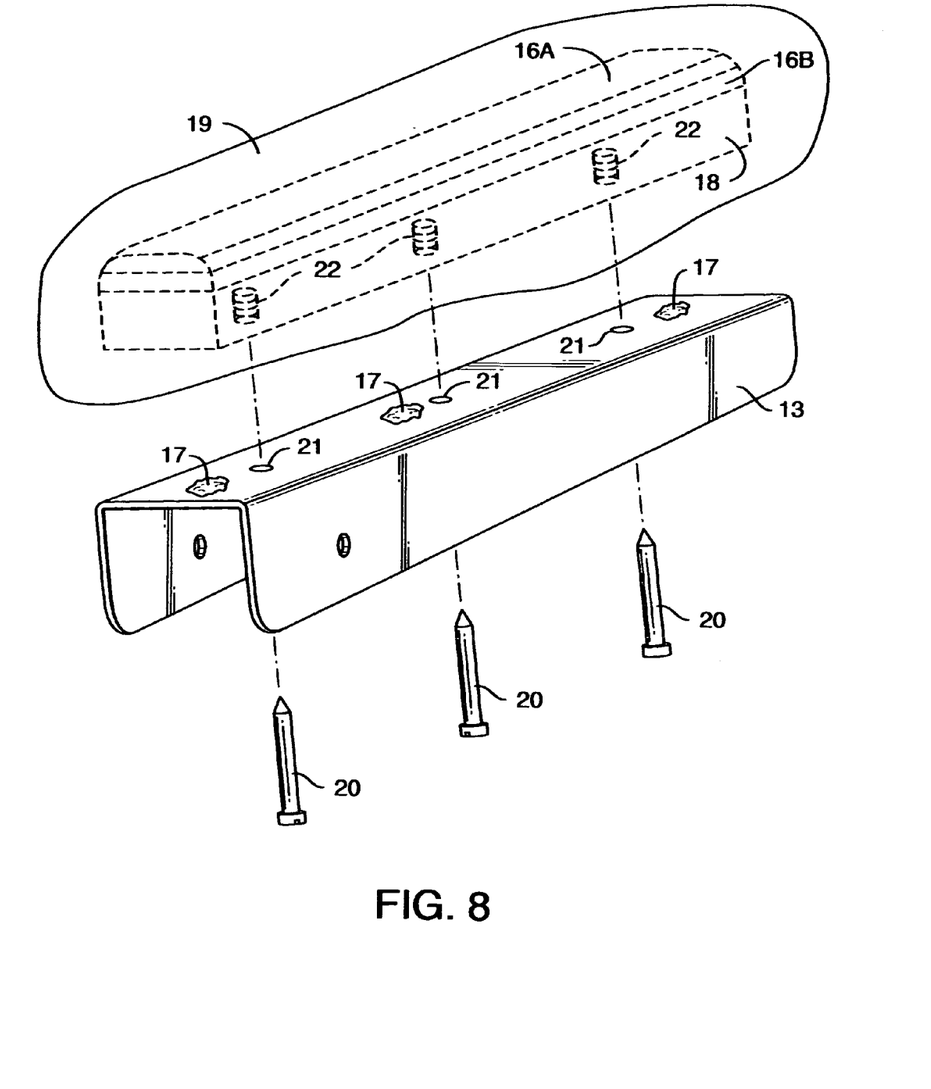
FIG. 8 is an exploded view of the third variant of the base unit cushion component of the invention in apposition to the pivotable handrest base unit.
Figure 9:
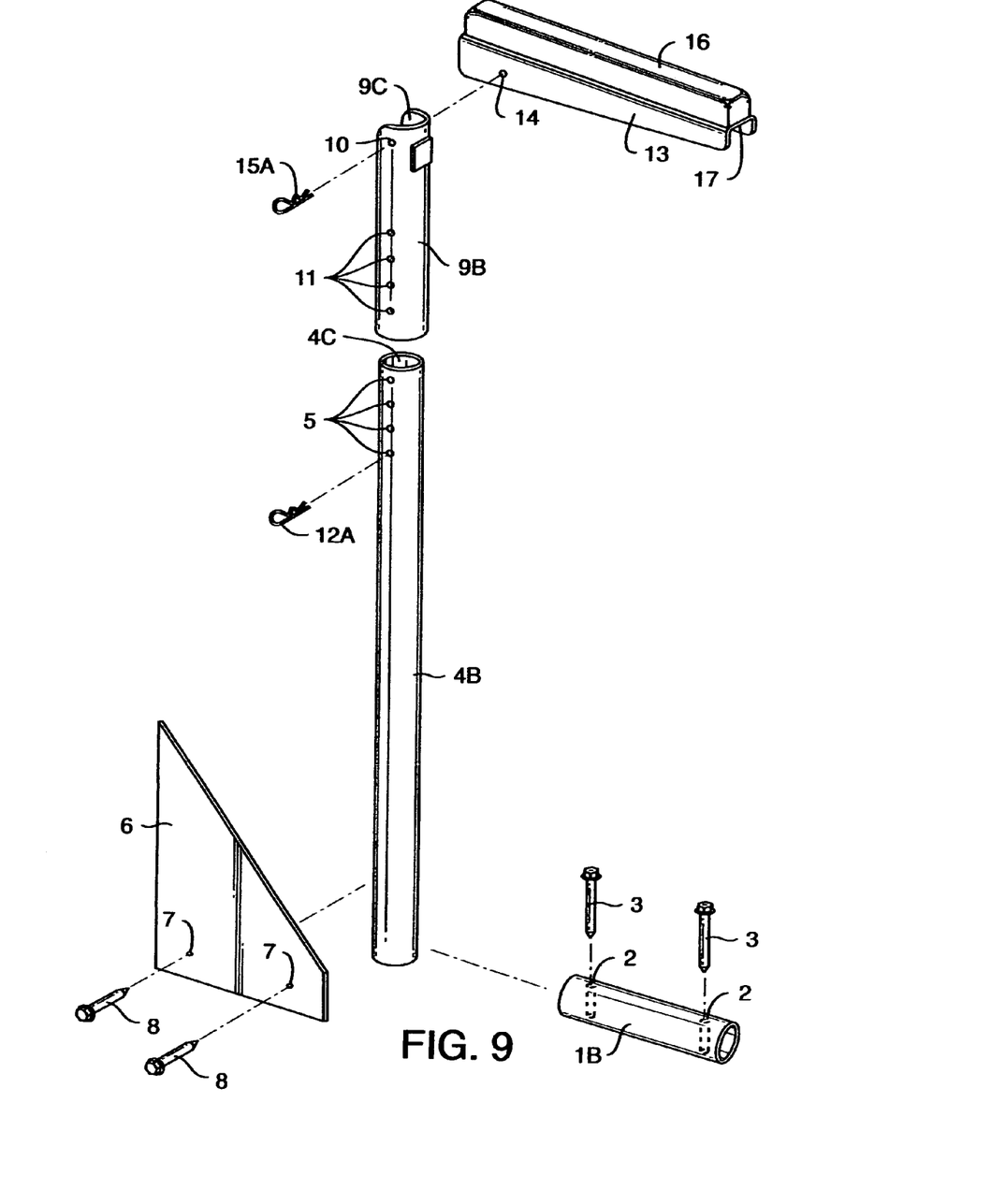
FIG. 9 is an exploded view of the various components of an alternate embodiment of the invention including the first variant of the base unit cushion component of the invention.

FIG. 1 depicts a zero turn lawnmower device A equipped with a pair of the invented mounting support arms affixed to the frame assembly portion B of device A. FIG. 2 shows the so-equipped device A in the presence of platform C atop of which is a person D disembarking from a wheelchair E in an effort to mount device A. FIG. 5 is an exploded view of the various component parts of the invented mounting support arm. FIGS. 3 and 4 each show an individual invented mounting support arm in fully assembled form. The invention features first and foremost a mounting tube unit 1 typically hollow and rectangularly shaped, though it could be hollow and cylindrically shaped as well. A cylindrically shaped mounting tube unit 1B is shown in FIG. 9. A plurality of concentrically aligned vertically inclined paired holes 2 in the topside and bottomside of tube unit 1 serve to vertically receive a first pair of self tapping screws 3 so as to thereby affix mounting tube unit 1 to the topside of one lateral portion of frame assembly B as shown in FIG. 4 with screws 3 insertable into holes drilled into the topside of the lateral portion of frame assembly B that are concentric with holes 2. A first rectangularly shaped hollow tube unit 4 is perpendicularly affixed to the posterior side of tube unit 1 as shown in FIG. 4. Such affixation is accomplished by way of, for example, gluing or welding units 1 and 4 together. A first plurality of oppositely positioned, concentrically aligned horizontally inclined paired holes 5 are located in each lateral side of tube unit 4 as shown in FIG. 5. Tube unit 4 could also be cylindrical in shape and be characterized by the presence of such holes 5 as well. A cylindrically shaped hollow tube unit 4B is shown in FIG. 9. Rectangular shaping is however the shaping mode of units 1 and 4 in respect of the preferred embodiment. Laterally positioned multisided mounting plate 6 is shown in FIGS. 3, 4 and 5. A horizontally inclined pair of through holes 7 in plate 6 serve to receive a second pair of self tapping screws 8 being durably inserted into holes 7 and into holes drilled into lateral walling of frame assembly B that are concentrically aligned with holes 7 as a means for affixing plate 6 to a lateral side of frame assembly B as shown in FIGS. 3 and 4. Plate 6 could also be affixed by way of welding or adhesively gluing it to the lateral side of frame assembly B as shown in FIGS. 3 and 4. Resort to FIG. 3 shows plate 6 affixed as well to both mounting tube unit 1 and first hollow tube unit 4. Such affixation is accomplished by way of welding or adhesively gluing plate 6 to units 1 and 4 respectively. There is a second rectangularly shaped hollow tube unit 9 with a diagonal breadth 9A in excess of the diagonal breadth 4A of unit 4 as can be seen with reference to FIG. 5. Once again, although rectangular shaping of unit 9 is a feature of the preferred embodiment of the invention, were a cylindrically shaped unit 9B to be resorted to as a complementing unit as respects a cylindrically shaped unit 4B then, the diametric breadth 9C of such a unit 9B would exceed that of, to wit, 4C such a unit 4B, all as seen in FIG. 9. A lower set of concentrically aligned, horizontally inclined holes 11 is found in unit 9. A height adjustment pin being either a cotter pin 12A or a detent pin 12 is insertable through holes 11 and any one pair of the first plurality of paired holes 5 in unit 4 after unit 9 is first slid over and about unit 4 in order to adjust the height of the mounted support arm for use by both taller or shorter persons D mounting a device A as shown in FIG. 2 or dismounting such a device A as well. A three sided pivotable handrest base unit 13 is affixed to and coplanarly pivotable about the uppermost portion of unit 9 by way of inserting the pivot pin complex through concentrically aligned paired horizontally inclined pivot pin holes 14 posteriorly positioned in unit 13 and in turn through an upper set of concentrically aligned, horizontally inclined holes 10 in unit 9 that are concentric as well with holes 14 all as can be noted with reference to FIG. 5. The pivot pin complex could be a cotter pin 15A or, a detent pin 15. Pins 12A and 15A are shown in FIG. 9. A first variant of a base unit cushion component 16; made up of a rubberlike or rubbery material is adhesively and non-removably affixable with, for example, glue 17 to the topside of handrest base unit 13 as can be noted with reference to FIG. 5. Alternatively, as shown in FIG. 7, a second variant of such a cushion is one made up of compressed layers of cloth material 16A or a spongy substance 16B or a combination of either, and positioned upon a rigid plate 18, with a durable wrap material element 19 wholly circumscribing such material 16A and/or 16B and likewise, also plate 18, with such component 16 being then permanently affixed to the topside of base unit 13 by way of a plurality of screws 20 bored into threaded holes 21 in the topside of unit 13 and threaded holes 22 in plate 18 with holes 21 and holes 22 being concentrically aligned and further also aligned as well with wrap holes 19A in wrap material element 19. The featured elements of this non-rubberized variant of cushion component 16 are shown in FIG. 7. Wrap material element 19 circumscribing material 16A and/or 16B and plate 18 is also merely adhesively and permanently affixable with glue 17 to the topside of base unit 13 as shown in FIG. 8.

Figure 6:
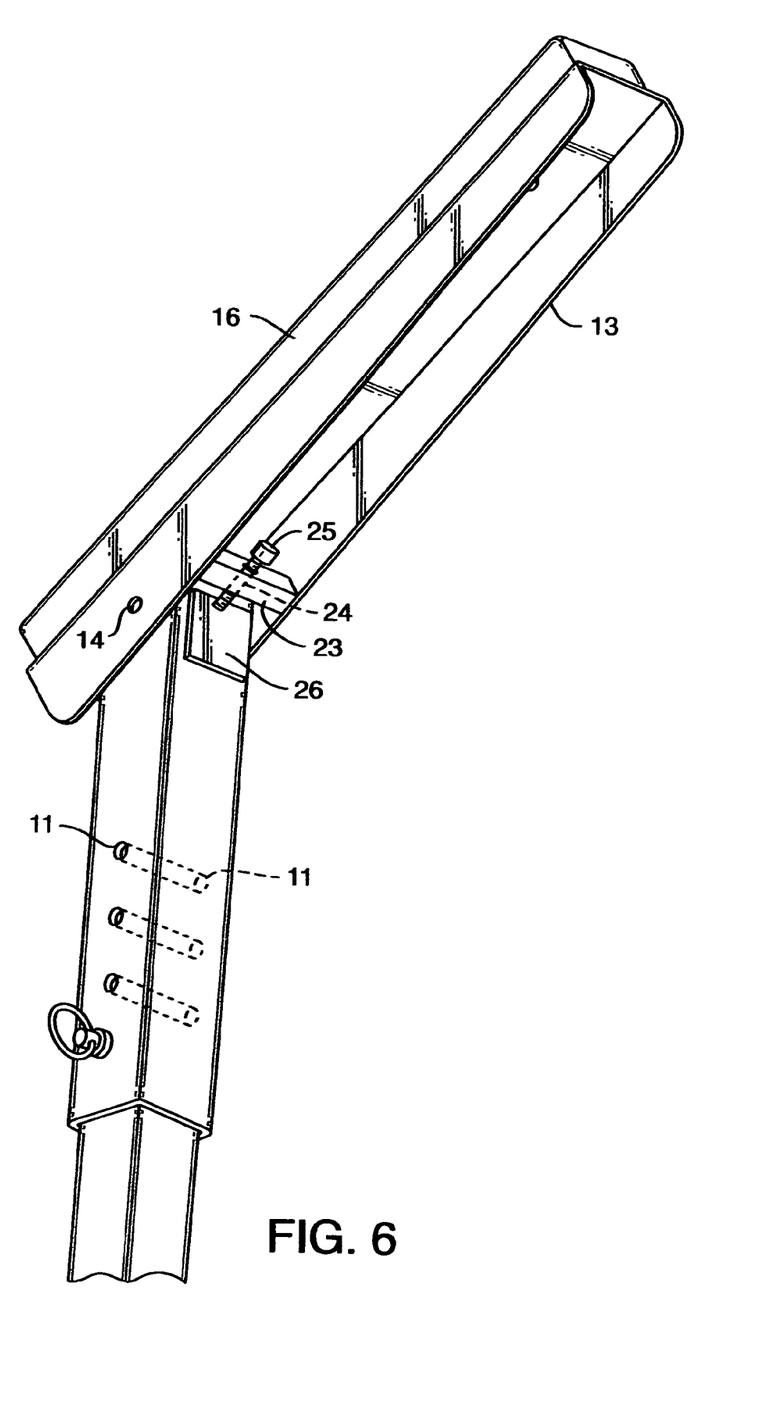
FIG. 6 is a bottom oriented perspective view showing the pivot arm stop complex of the invention affixed within the pivotable handrest base unit thereof.

Finally, affixed by welding to the interior walling of the two lateral sides of handrest base unit 13 near the posterior end thereof, is a small rectangularly shaped plate unit 23 within which there is a threaded hole 24 centrally positioned for receipt of a threaded bolt unit 25 that is threadably adjustable with unit 23, hole 24 and unit 25 being together a pivot arm stop complex such as can be seen with reference to FIG. 6. The pivot arm stop complex serves to facilitate static positioning of base unit 13 at various angles with respect to the horizontally positioned lie of the apical portion of unit 9. Variability of such static positioning is accomplished by way of simply screwing bolt 25 within hole 24 through a distance requisite to achieving a given desired angular lie of unit 13. Retardation of pivotability downward at such a desired angular lie in respect of such state of static positioning is accomplished by way of simply screwing bolt 25 within hole 24 until some portion of the end of bolt 25 finally touches the front facial portion of unit 9 or so touches an optional face plate 26 affixed thereto as seen in FIG. 6. In this way, unit 13 can be coplanarly, with reference to the plane defined by the frontal side of unit 9 and perpendicularly defined outward extensions therefrom, pivotable about the apical portion of unit 9 and can accordingly lie vertically upward therefrom as is shown reference to FIG. 6 or it can lie horizontally thereto as is shown in FIG. 4 or somewhere between either position per the wishes of a user person D. Vertical positioning of base unit 13 upright without regard to any adjustment of bolt unit 25 of the stop complex allows for a mower unit A equipped with two equivalent embodiments of the invention to be driven further below a platform C. Horizontal or near horizontal positioning resulting with resort to appropriate adjustment of bolt unit 25 serves to accommodate the particular positioning preferences of any user D when placing his or her hand about cushion 16 while mounting or dismounting unit A. This pivot arm stop complex feature of the invention is, respectfully stated, a truly innovative and unique feature of the invention in respect of the overall functionality of the invention.

In conclusion, respectfully submitted, the invention as described above is, respectfully submitted, not only new and unique but unquestionably useful, especially in terms of facilitating any mounting and dismounting of riding lawnmowers by persons suffering from generalized lower body weakness brought on by adverse neurological conditions.

What is claimed is:

1. A zero turn lawnmower mounting support arm, comprising:
   a. a mounting tube unit;
   b. a plurality of concentrically aligned vertically inclined paired holes within said mounting tube unit;
   c. a first pair of self-tapping screws insertable one each into one each of said plurality of concentrically aligned vertically inclined paired holes and concentrically drilled holes within a topside of a lateral portion of a frame assembly portion of a zero turn lawnmower;
   d. a first hollow tube unit perpendicularly affixed by welding to a posterior side of said mounting tube unit;
   e. a first plurality of concentrically aligned horizontally paired holes within respectively oppositely positioned locations in each lateral side of said first hollow tube unit;
   f. a laterally positioned multisided mounting plate;
   g. a horizontally inclined pair of through holes in said mounting plate;
   h. a second pair of self-tapping screws insertable one each, into each of said horizontally inclined pair of through holes and corresponding holes drilled into lateral walling of said frame assembly portion for affixation of said mounting plate to said frame assembly portion;
   i. said mounting plate being further affixed by welding to said mounting tube unit and said first hollow tube unit;
   j. a second hollow tube unit;
   k. said second hollow tube unit having an internal breadth in excess of an overall breadth of said first hollow tube unit and being accordingly receivable about said first hollow tube unit;
   l. an upper set of concentrically aligned horizontally inclined holes in said second hollow tube unit;
   m. a lower set of concentrically aligned horizontally inclined holes in said second hollow tube unit;
   n. a height adjustment pin insertable through said lower set of concentrically aligned horizontally inclined holes and any one set of said first plurality of concentrically aligned horizontally inclined paired holes;
   o. a three-sided pivotable handrest base unit;
   p. a concentrically aligned set of paired horizontally inclined pivot pin holes in said handrest base unit near a posterior end thereof;
   q. a pivot pin complex insertable through said pivot pin holes and said upper set of concentrically aligned, horizontally inclined holes in coplanarly pivotable connection of said handrest base unit to said second hollow tube unit;
   r. a base unit cushion component being made up of a soft material resting upon a rigid plate all wholly circumscribed by a durable wrap material element;
   s. said wrap element being adhesively affixed permanently with glue at a bottomside thereof to a topside of said handrest base unit;
   t. a rectangularly shaped plate unit affixed at lateral sides thereof to interior walling of lateral sides of said handrest base unit near a posterior end of said base unit;
   u. a centrally positioned threaded hole within said plate unit, and;
   v. a threaded-bolt rotatably receivable by said threaded hole.

2. The zero turn lawnmower mounting support arm of claim 1 whereby, affixation of said rectangularly shaped plate unit is accomplished by way of welding said plate unit at said lateral sides thereof to said interior walling.

3. The zero turn lawnmower mounting support arm of claim 1 whereby, affixation of said rectangularly shaped plate unit is accomplished by way of gluing said plate unit at said lateral sides thereof to said interior walling.

4. A zero turn lawnmower mounting support arm, comprising:
   a. a mounting tube unit;
   b. a plurality of concentrically aligned vertically inclined paired holes within said mounting tube unit;
   c. a first pair of self-tapping screws insertable one each into one each of said plurality of concentrically aligned vertically inclined paired holes and concentrically drilled holes within a topside of a lateral portion of a frame assembly portion of a zero turn lawnmower;
   d. a first hollow tube unit perpendicularly affixed by welding to a posterior side of said mounting tube unit;
   e. a first plurality of concentrically aligned horizontally paired holes within respectively oppositely positioned locations in each lateral side of said first hollow tube unit;
   f. a laterally positioned multisided mounting plate;
   g. a horizontally inclined pair of through holes in said mounting plate;
   h. a second pair of self-tapping screws insertable one each, into each of said horizontally inclined pair of through holes and corresponding holes drilled into lateral walling of said frame assembly portion for affixation of said mounting plate to said frame assembly portion;
   i. said mounting plate being further affixed by welding to said mounting tube unit and said first hollow tube unit;
   j. a second hollow tube unit;
   k. said second hollow tube unit having an internal breadth in excess of an overall breadth of said first hollow tube unit and being accordingly receivable about said first hollow tube unit;
   l. an upper set of concentrically aligned horizontally inclined holes in said second hollow tube unit;
   m. a lower set of concentrically aligned horizontally inclined holes in said second hollow tube unit;
   n. a height adjustment pin insertable through said lower set of concentrically aligned horizontally inclined holes and any one set of said first plurality of concentrically aligned horizontally inclined paired holes;
   o. a three-sided pivotable handrest base unit;
   p. a concentrically aligned set of paired horizontally inclined pivot pin holes in said handrest base unit near a posterior end thereof;

q. a pivot pin complex insertable through said pivot pin holes and said upper set of concentrically aligned, horizontally inclined holes in coplanarly pivotable connection of said handrest base unit to said second hollow tube unit;
r. a base unit cushion component being made up of a soft material resting upon a rigid plate all wholly circumscribed by a durable wrap material element with a plurality of holes in said wrap material element concentric with an equivalent plurality of threaded holes in said rigid plate;
s. a plurality of threaded holes in a topside of said handrest base unit concentric with said plurality of holes in said rigid plate;
t. screws receivable by said holes in said topside of said handrest base unit and said holes in said wrap material element and said holes in said rigid plate for permanent affixation of said base unit cushion component to said handrest base unit;
u. a rectangularly shaped plate unit affixed at lateral sides thereof to interior walling of lateral sides of said handrest base unit near a posterior end of said base unit;
v. a centrally positioned threaded hole within said plate unit, and;
w. a threaded bolt rotatably receivable by said threaded hole.

5. The zero turn lawnmower mounting support arm of claim 4, whereby, said mounting tube unit, said first hollow tube unit and said second hollow tube unit are all rectangularly shaped.

6. The zero turn lawnmower mounting support arm of claim 4, whereby, said mounting tube unit, said first hollow tube unit and said second hollow tube unit are all cylindrically shaped.

7. The zero turn lawnmower mounting support arm of claim 4, whereby, said pivot pin complex is a cotter pin.

8. The zero tarn lawnmower mounting support arm of claim 4, whereby, said pivot pin complex is a detent pin.

9. The zero turn lawnmower mounting support arm of claim 4 whereby, said height adjustment pin is a cotter pin.

10. The zero turn lawnmower mounting support arm of claim 4 whereby, said height adjustment pin is a detent pin.

11. The zero turn lawnmower mounting support arm of claim 4 whereby, affixation of said rectangularly shaped plate unit is accomplished by way of welding said plate unit at said lateral sides thereof to said interior walling.

12. The zero turn lawnmower mounting support arm of claim 4 whereby, affixation of said rectangularly shaped plate unit is accomplished by way of gluing said plate unit at said lateral sides thereof to said interior walling.

* * * * *